United States Patent [19]
McKinney et al.

[11] 4,107,526
[45] Aug. 15, 1978

[54] ION SCATTERING SPECTROMETER WITH MODIFIED BIAS

[75] Inventors: James T. McKinney, Stillwater; Thomas W. Rusch, Falcon Heights, both of Minn.

[73] Assignee: Minnesota Mining and Manufacturing Company, St. Paul, Minn.

[21] Appl. No.: 758,836

[22] Filed: Jan. 12, 1977

Related U.S. Application Data

[63] Continuation-in-part of Ser. No. 669,091, Mar. 22, 1976, abandoned.

[51] Int. Cl.² .............................................. H01J 35/00
[52] U.S. Cl. ..................................... 250/305; 250/309
[58] Field of Search .............. 250/309, 305, 396, 397, 250/398

[56] References Cited

U.S. PATENT DOCUMENTS

| | | | |
|---|---|---|---|
| 3,735,128 | 5/1973 | Palmberg | 250/305 |
| 3,742,214 | 6/1973 | Helmer et al. | 250/305 |
| 3,916,190 | 10/1975 | Valentine et al. | 250/305 |
| 3,939,344 | 2/1976 | McKinney | 250/309 |

Primary Examiner—Alfred E. Smith
Assistant Examiner—B. C. Anderson
Attorney, Agent, or Firm—Cruzan Alexander; Donald M. Sell; William B. Barte

[57] ABSTRACT

An ion scattering spectrometer (ISS) providing enhanced sensitivity, reduced background, and preferential detection of low-mass scattered ions over that of high-mass sputtered ions is disclosed. These advantages are accomplished by a biasing arrangement which maintains a potential difference between the analyzer exit and the detector input at less than 30 volts and substantially eliminates the high potential provided on detector inputs of prior art ion scattering spectrometers which attracted and thereby accelerated ions prior to impinging on the inputs.

10 Claims, 4 Drawing Figures

ION SCATTERING SPECTROMETER WITH MODIFIED BIAS

CROSS-REFERENCE TO RELATED APPLICATION

This application is a C.I.P. of patent application Ser. No. 669,091, filed Mar. 22, 1976, now abandoned.

BACKGROUND OF THE INVENTION (1) Field of the Invention

This invention relates to spectrometers adapted for the analysis of surfaces in which ions indicative of the surface composition are detected. In particular, such spectrometers preferably infer the composition of the surface from a determination of the decrease in a kinetic parameter such as energy associated with ions scattered off the surface.

(2) Description of the Prior Art

Various techniques and apparatus for analyzing surfaces by scattering ions from the surfaces are disclosed in U.S. Pat. Nos. 3,480,774, issued to Smith on Nov. 25, 1969, 3,665,182 issued to Goff and Smith on May 23, 1972 and 3,665,185, issued to Goff on May 23, 1972. Such techniques include impinging a primary ion beam on a sample. The energy of the ions scattered at a given angle is thereafter measured and the intensity of a signal associated with the measured scattered ions is plotted as a function of the ratio of energy of the scattered ions to that of the impinging ions (i.e., $E_1/E_o$) to at least semi-quantitatively identify the elemental composition of the bombarded surface. In the techniques disclosed in these patents, signals resulting from the passage of sputtered ions through the energy analyzer have generally been observed and measured, even when neutralization of surface charge buildup is achieved. The presence of the signal generally attributed to sputtered ions decreases the overall signal-to-noise ratio, and obscures the detection of scattered ions having a low ratio of $E_1/E_o$, which low ratios correspond to those ions that have lost a large fraction of their incident energy as a result of being scattered from surface elements of relatively low atomic mass.

SUMMARY OF THE INVENTION

The ion scattering spectrometer (ISS) of the present invention generally includes a support for a specimen, a surface of which is to be analyzed, means, such as an ion gun, for directing a beam of ions having a preselected atomic mass and a single preselected energy toward the surface, analyzing means for passing ions having a selected energy, and detecting means including a material having an electron emissive surface for receiving and detecting the passed ions and for converting an ion current associated therewith into a corresponding electron signal. The analyzing means, such as, for example, an electrostatic sector or cylindrical mirror analyzer includes an entrance section for receiving ions from the specimen surface, an analyzing section for selecting such ions passing through the entrance section at a given angle with respect to the ion beam directed toward the specimen surface and having a predetermined energy and an exit section for passing the selected ions.

The improvement of the present invention lies in the manner in which the detecting means is operated with respect to the analyzing means. In prior art devices, the detecting means was operated at potentials such that ions passed by the analyzing means were pre-accelerated prior to impinging on the detector. In this manner, the probability of detecting incident ions was substantially independent of the energy of those ions. However, such a mode of operation has now been found to result in the production of spurious noise and in a decreased probability of detection of those ions properly passed by the analyzing means. In the present invention, the detecting means is electrically biased with respect to the analyzing means such that the electron emissive surface is maintained at a potential within 30 volts of that maintained in the exit section of the analyzing means.

In the present invention, this biasing arrangement results in the following improvements: first, by proper selection of a lower voltage at the input to the detecting means, as opposed to the high negative voltage thus applied in prior art devices, the energy of the incident ions is controlled such that the variation in the efficiency with which secondary electrons are produced in response to ion bombardment as a function of the mass of the ion results in the preferential detection of low-mass scattered ions having relatively high velocities over high mass sputtered ions having relatively low velocities.

Second, the maintenance of the potential within 30 volts results in the absence of a force tending to attract electrons emitted from the emissive surface toward the analyzing means and results in more of these electrons being contained within the detecting means, resulting in more efficient detection of ions properly passed by the analyzing means and in an appreciably stronger electron signal corresponding to the detected ions.

Third, such a low potential also results in the absence of a force tending to attract ions having an energy outside the pass-band of the analyzing means and results in a reduction in the background of the electron signal.

In one embodiment, an equipotential region is established by maintaining the exit section of the analyzing means and the ion receptive electron emissive surface of the detecting means at the same potential, such as at ground potential. In another embodiment, the emissive section is maintained approximately 20 volts negative with respect to the exit section such that low energy electrons passed through the exit section are repelled from the emissive surface.

In an alternative embodiment, the potentials applied to various sections of the analyzing means and those applied to the detecting means are such that ions passed through the analyzing means into the detecting means have an energy consistent with the preferential detection of the lower mass ions.

DESCRIPTION OF THE PREFERRED EMBODIMENTS

Figure 1:
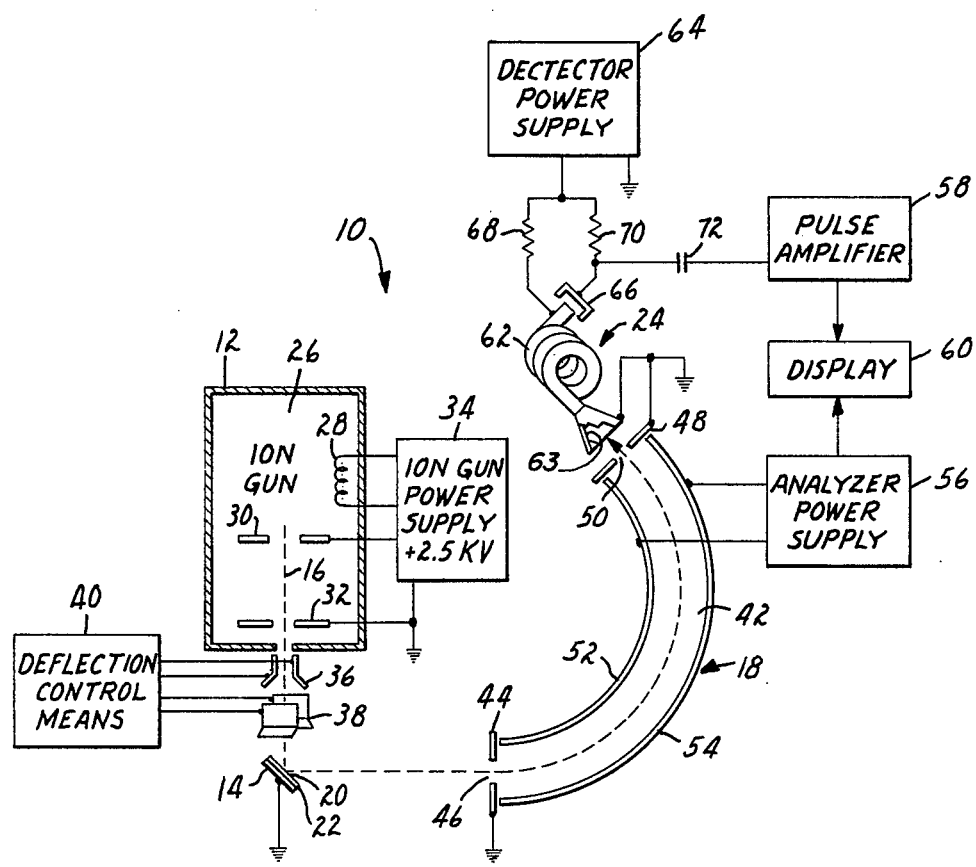
FIG. 1 is a combined cross sectional view and block diagram of one embodiment of the spectrometer of the present invention.

FIG. 1 shows a compact elemental analyzing apparatus 10 comprising an ion generating means 12 which produces and directs a beam of noble gas ions having a preselected atomic mass and a preselected energy, a specimen support 14 which is positioned in the path of the beam of ions 16, analyzing means, such as an electrostatic analyzer 18 for receiving ions from a surface 20 of a specimen 22 and for passing such received ions as have a selected energy and means such as a detector 24 providing secondary electrons in response to ion bombardment for detecting ions passed by the analyzing means 18 and for converting an ion current associated therewith into a corresponding electronic signal.

Figure 2:
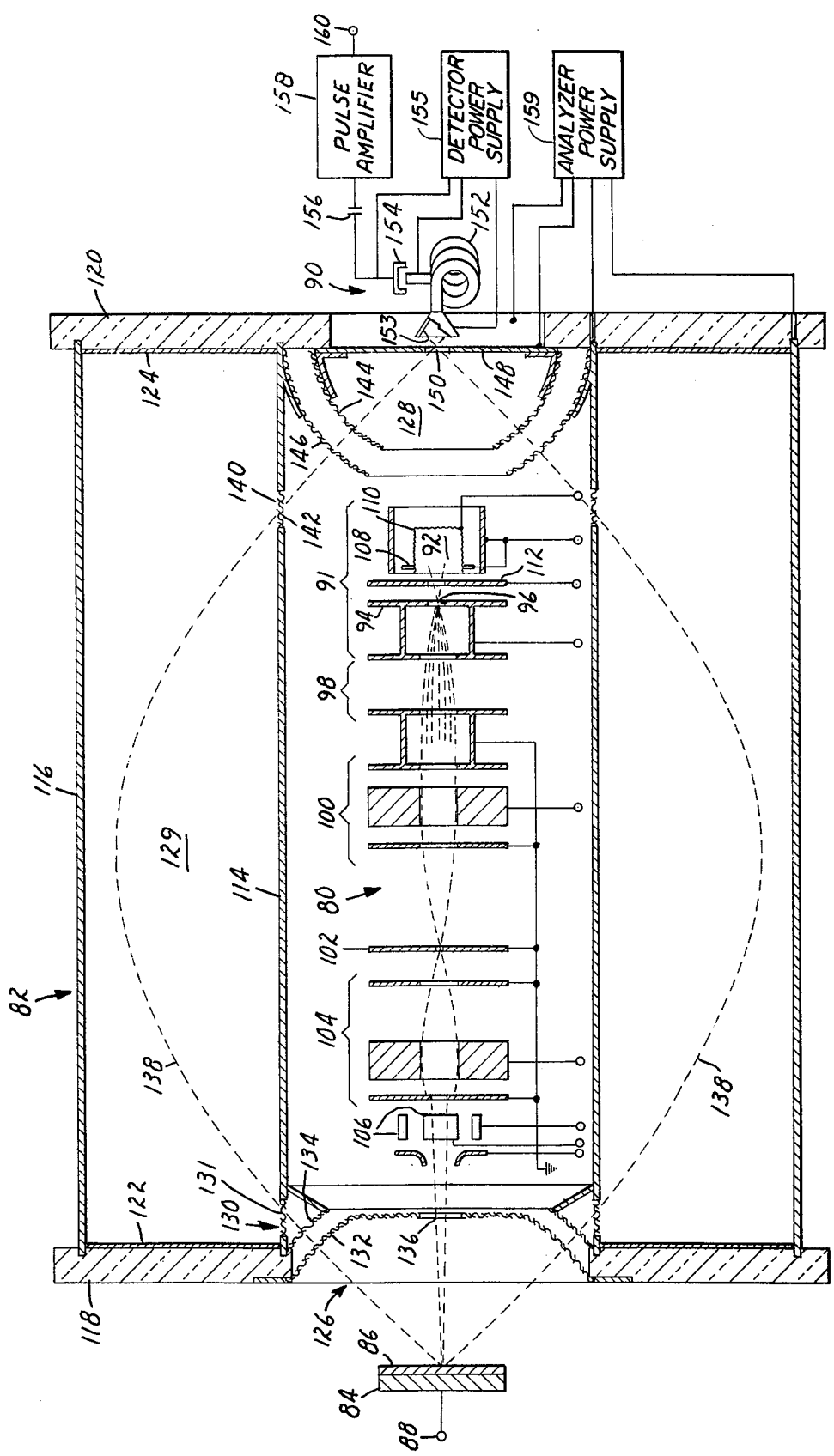
FIG. 2 is a combined cross sectional view and block diagram of another embodiment of the spectrometer of the present invention.

The ion generating means 12 is substantially the same as that set forth as FIG. 2 in U.S. Pat. No. 3,665,182, the disclosure of which is incorporated herein by reference. In addition to numerous apertures and electrodes, many of which for purposes of simplicity are not shown in FIG. 1, the ion generating means 12 comprises an ion gun 26 having an electron bombardment source 28 and acceleration electrodes 30 and 32. The electron bombardment source 28 and electrodes 30 and 32 are coupled to a suitable ion gun power supply 34 in the manner set forth in the above-referenced patent. Deflection electrodes 36 and 38, together with the deflection control means 40, enable scanning the beam 16 about a predetermined area of the sample 22, thereby causing the ion beam to impinge upon the surface 20 about the predetermined area such that the impinging primary ions are scattered therefrom, and such that scattered ions enter the entrance slit 46 of the analyzer 42.

The specimen support 14 is shown for simplicity to support a single specimen 22, the surface 20 of which is to be analyzed. As set forth in the above-referenced patent, the support may be provided with means for positioning a number of specimens and to be movable, enabling each of the specimens to be positioned in the path of the ion beam 16. Various types of similar supports for positioning multiple specimens may likewise be provided. Alternatively, larger specimens may be mounted singly on a movable specimen support such that various areas of the larger specimens may be analyzed.

In the embodiment of FIG. 1, the energy analyzer 18 is preferably a conventional 127° electrostatic energy analyzer 42, which analyzer includes an entrance section comprising diaphragm 44 having a rectangular entrance slit 46, an exit section comprising diaphragm 48 having a rectangular exit slit 50 and an analyzer section comprising two curved electrostatic analyzer plates 52 and 54, respectively, which plates preferably have a mean radius of approximately 5.1 cm. The entrance and exit diaphragms 44 and 48, respectively, may be grounded as shown or may be biased by a power supply if desired. The entrance and exit slits 46 and 50, respectively, have a preferred width of 0.250 millimeter. The entrance diaphragm 44 is spaced about 1 centimeter from the surface 20 of the specimen 22 being analyzed.

The detecting means 24 preferably includes a continuous channel electron multiplier 62 having a body including an electron emissive surface 63 forming a continuous dynode, a high voltage detector power supply 64 for powering the multiplier, and an electron collector 66. The multiplier 62 preferably has an 8 millimeter entrance cone, which encompasses the entire exit area along the axis extending from the exit slit 50 of the analyzer 42. Such a multiplier is commercially available as Model No. CEM 4028, manufactured by Galileo Electro Optics Corporation, Galileo Park, Sturbridge, Massachusetts 01581. Similarly, electron multipliers having discrete dynodes in which each dynode includes a material having an electron emissive surface and in which successive dynodes are positioned to receive and amplify secondary electrons, may also be used. A capacitor 72 is provided for AC coupling the electronic signal from the collector 66 to a conventional pulse amplifier 58, and thence to the display 60.

The ion gun 26 and the associated deflection electrodes 36 and 38, together with the specimen support 14, and appropriate portions of the analyzer 18 and the detector 24 are adapted to be included within an evacuatable chamber (not shown). In operation, such a chamber is typically evacuated to a pressure of less than $10^{-5}$ Pascal. A getter and a cryopanel (also not shown) are preferably included within the chamber to additionally remove the active gases remaining in the chamber. The pumping of inert gases is discontinued and a gas or a mixture of gases such as a noble gas is then released into the chamber until the static pressure is increased to approximately $7 \times 10^{-3}$ Pascal. Thereafter, all openings to the chamber are closed, and the electron emitter 28 is energized to ionize the gas atmosphere within the chamber. Application of suitable potentials to the filament 28, to the electrodes 30 and 32 and to the other electrodes (not shown) accelerates electrons produced by the filament 28 to ionize gas in the chamber. By maintaining the acceleration electrode 32 at approximately ground potential and the first electrode 30 at a potential positive with respect to ground, a monoenergetic beam of noble gas ions 16 is extracted through the electrodes 30 and 32, having an energy approximately equal to the potential provided between the electrodes 30 and 32. This beam of noble gas ions is then utilized to analyze the composition of the surface of a specimen 22. The gas preferably used in the present invention may be any noble gas; particularly helium, neon, and argon are commonly used. Insulated electrical feedthroughs and connectors are similarly provided to connect the components within the chamber and the electrical apparatus, power supplies and the like located outside the chamber.

In order to analyze the energy of ions entering the entrance slit 46, the analyzer plates 52 and 54 of the analyzer 42 are connected to the output from an analyzer power supply 56. This power supply permits a suitable potential to be applied to the plates 52 and 54 to direct ions having a predetermined energy through the exit slit 50 of the exit diaphragm 48.

In the present invention, the entrance to the multiplier 62 and the exit diaphragm 48 are preferably coupled together and maintained at ground potential, while the exit portion of the multiplier 62 and the electron collector 66 are biased positively through biasing resistors 68 and 70, respectively, via a positive potential from the detector power supply 64.

The ions passed by the analyzer 42 are detected and converted by the detector 24 into an electron signal corresponding to the current of passed ions. This signal is coupled through capacitor 72 to the pulse amplifier 58 and thence to the display 60, which also receives a signal from the analyzer power supply 56 so as to enable a spectrum to be displayed which corresponds to a plot of the magnitude of the scattered ion signal having a given amount of energy loss as a function of the ratio of the energy after scattering to the initial energy of the initial ion beam (i.e., $E_1/E_o$).

Numerous advantages are obtained by the biasing arrangement set forth hereinabove. These advantages are best appreciated in conjunction with the discussion of FIGS. 3 and 4 set forth hereinafter.

Another embodiment of the spectrometer of the present invention is shown in a combined cross sectional view and block diagram of FIG. 2. In this figure, an ion gun shown generally as 80 is axially positioned within an electrostatic cylindrical mirror analyzer shown generally as 82. A specimen mounting means 84 positions a specimen 86 in axial alignment with the ion gun 80 and the analyzer 82. A terminal 88 is also provided on the specimen mounting means 84 such that the specimen may be maintained at a desired electrical potential. Axially mounted at the opposite end of the analyzer 82 is a detecting means 90, which means is substantially the same as that shown in FIG. 1.

The ion gun 80 is substantially the same as that recited and claimed in U.S. Pat. No. 3,937,958, the disclosure of which is incorporated herein by reference. This gun is generally of the electron bombardment type and includes an ion generating portion 91 having a source of charged particles shown generally as 92 and a primary extractor electrode 94 having an aperture 96. The aperture 96 controls the passage of ions from the source and thus defines the effective diameter of the generated beam. Sequentially positioned downstream of the generator 91 is an acceleration section shown generally as 98, a first focusing lens 100, a diameter limiting electrode 102, a second focusing lens 104 and deflection electrodes 106. The ion generator portion 91 includes a source of electrons 108, an electron permeable cylindrical grid 110 and a supplemental extractor electrode 112. The electron source 108 is a cylindrical single turn filament which encircles the cylindrical grid 110 and which lies in a plane approximately normal to the axis of the beam.

As set forth in U.S. Pat. No. 3,937,958, upon evacuation of the chamber (not shown) in which the above described apparatus is positioned, and backfilling the evacuated chamber with a partial pressure of a noble gas, the application of suitable potentials to the various portions of the gun 80 causes gas within the cylinder 110 to be ionized. The application of other suitable potentials to the acceleration portion 98 causes these ions to be extracted from the ion generating portion 91 into a beam of ions having parallel trajectories. These ions are subsequently focused by the first and second focusing lenses 100 and 104, respectively, so as to cause a focused beam to impinge upon the specimen 86.

The cylindrical mirror analyzer 82 is constructed to have inner and outer concentric cylindrical electrodes 114 and 116, respectively. These electrodes are formed of stainless steel tubing in a conventional manner. The ends of the cylinders are secured in ceramic endplates 118 and 120 so as to maintain the desired concentricity. The ceramic endplates 118 and 120, in addition to being shaped to receive the cylindrical electrodes 114 and 116, are provided with graphite or other resistive coatings 122 and 124 on the inward facing surfaces thereof such that a potential applied between the inner and outer electrodes 114 and 116 is distributed across the resistive surfaces to provide a field gradient between the inner and outer electrodes in the region of the endplates 118 and 120 which is substantially identical to that provided by infinitely long electrodes. Such a configuration minimizes deviations in the analyzer performance and greatly facilitates the theoretical design of the analyzer.

The analyzer 82 is provided with an entrance section shown generally as 126, an exit section shown generally as 128 and an analyzing section shown generally as 129. The entrance section 126 includes a cylindrical aperture 130 in the wall of the inner cylinder 114 fitted with a fine mesh metal screen 131 to provide an equipotential surface across the aperture 130 through which the ions enter into the region between the inner and outer cylindrical electrodes. This surface thus suppresses field distortion in the analyzer section. The surface of the specimen 86 is positioned with respect to the aperture 130 such that ions scattered through about 137° from the axis of the ion beam are allowed to pass through the aperture 130. Preferably, the entrance section 126 additionally includes a second cylindrical metal screen 132 which is positioned proximate to and electrically insulated from the first screen 131, thus forming a region between the two screens in which a field may be generated by the application of potentials to the screens. This controls the energy of ions passing through the entrance section 126 and shields the surface of the specimen 86 from fields emanating from the first screen 131 and inner cylinder 114, thereby maintaining a substantially field-free region at the specimen surface.

In order to provide additional control of the fields between the surface of the specimen 86 and the first screen 131, it is preferable to provide electrodes such that no substantial non-radial field gradients with respect to the point of impingement exist in this region. Accordingly, it is further desirable to provide a third metal screen 134 interposed between the first and second screens 131 and 132, which third screen is electrically connected to the first screen 131, the second and third screens being concentric and substantially parallel to each other. To provide uniform radial fields, it is desirable that the second and third screens be substantially concentric spherical sections, having a common center point located where the primary ion beam impinges on the specimen surface. The second screen 132 is provided with an axially centered aperture 136 through which the ion beam from the ion gun 80 passes to impinge upon the surface of the specimen 86.

Ions scattered from the surface of the specimen 86 enter the analyzer section 129 between the inner and outer cylinders 114 and 116 along trajectories 138, and under the control of potentials applied between the inner and outer electrodes pass to the exit section 128 of the analyzer. This section includes a second cylindrical aperture 140 through the wall of the inner electrode 114, thereby allowing ions along the trajectories 138 to pass through the aperture and toward the exit from the analyzer. The aperture 140 is fitted with a fourth metal screen 142 which assumes the potential of the inner cylindrical electrode to provide an equipotential surface across the aperture 140 through which the ions exit and thereby further suppresses field distortion in the analyzer section 129. The exit section 128 further includes a fifth metal screen 144 axially symmetric and proximate to the screen 142 forming an axially symmetric aperture through which ions may pass and by which equipotential may be established across the aperture. A final metal screen 146 is also interposed between the fourth and fifth screens, concentric with and parallel to the screen 144. The screen 146 is electrically coupled to the screen 140 to thereby enable further control over the electric fields in the vicinity of the exit portion of the analyzer.

Screens 144 and 146 are preferably concentric spherical sections, having a common center point located at the plane of an axially positioned aperture 150 in the exit aperture plate 148. The aperture 150 allows ions along the trajectory 138 to cross over in the plane of the aperture plate 148 and thereafter enter the detector 90.

The detector 90 includes a continuous channel electron multiplier 152 comprising material having an electron emissive surface 153 and an electron collector 154, the output of which is coupled through a capacitor 156 to a pulse amplifier 158 and thence via output terminal 160 to suitable display apparatus (not shown).

In one embodiment, the exit aperture plate 148 and the entrance to the channel multiplier 152 are both maintained at ground potential, with the output of the multiplier 152 biased at several thousand volts positive potential by the detector power supply 155. The electron collector 154 is similarly biased at a positive potential by the supply 155 such that the electronic signal generated in the collector 154 is coupled via the capacitor 156 to the pulse amplifier 158. In this embodiment, the specimen holder 84 is similarly maintained approximately at ground potential. In order to analyze scattered ions over a range of ion energies from 0 to 2.5 KeV, the potential between the inner and outer electrodes 114 and 116 is sequentially varied over a range of potentials from 0 to 1.25 KV by an analyzer power supply 159 in the same manner as that disclosed in conjunction with FIG. 1.

Figure 3:
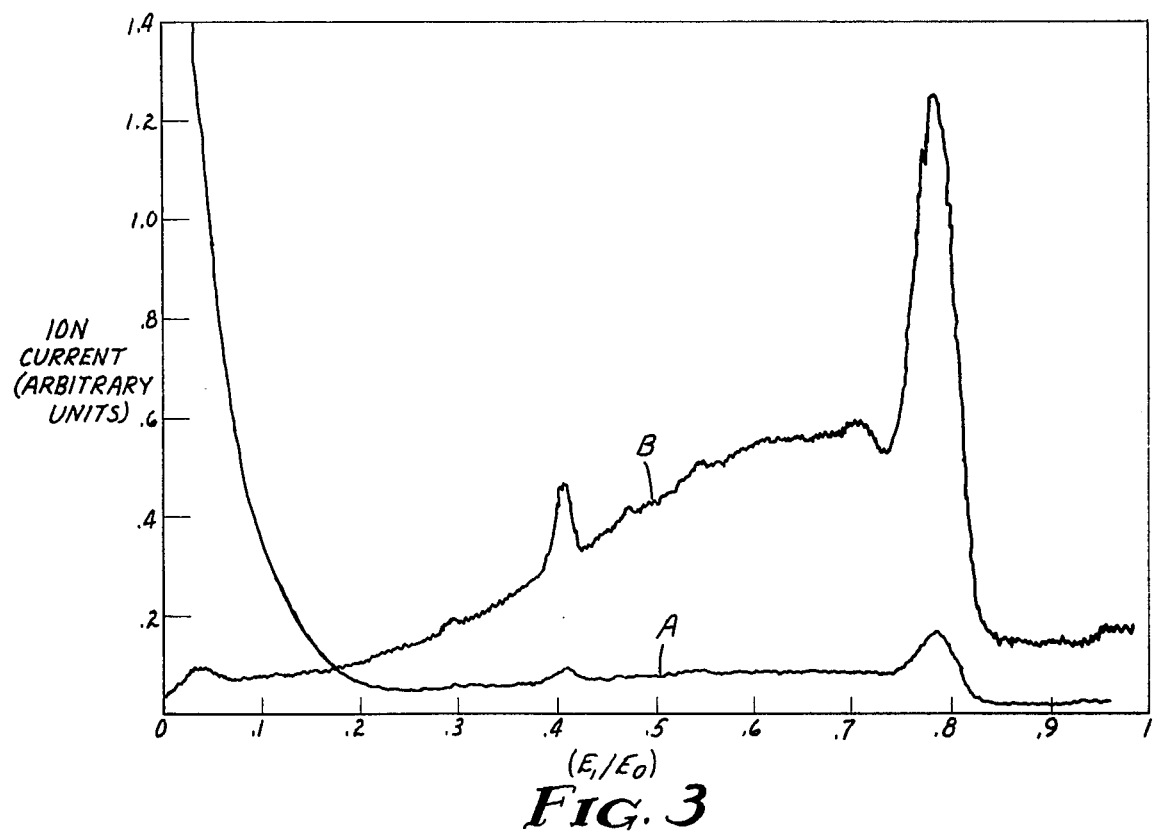
FIGS. 3 and 4 are illustrative spectra obtained from a prior art spectrometer and from a spectrometer similar to that shown in FIG. 2.
Figure 4:
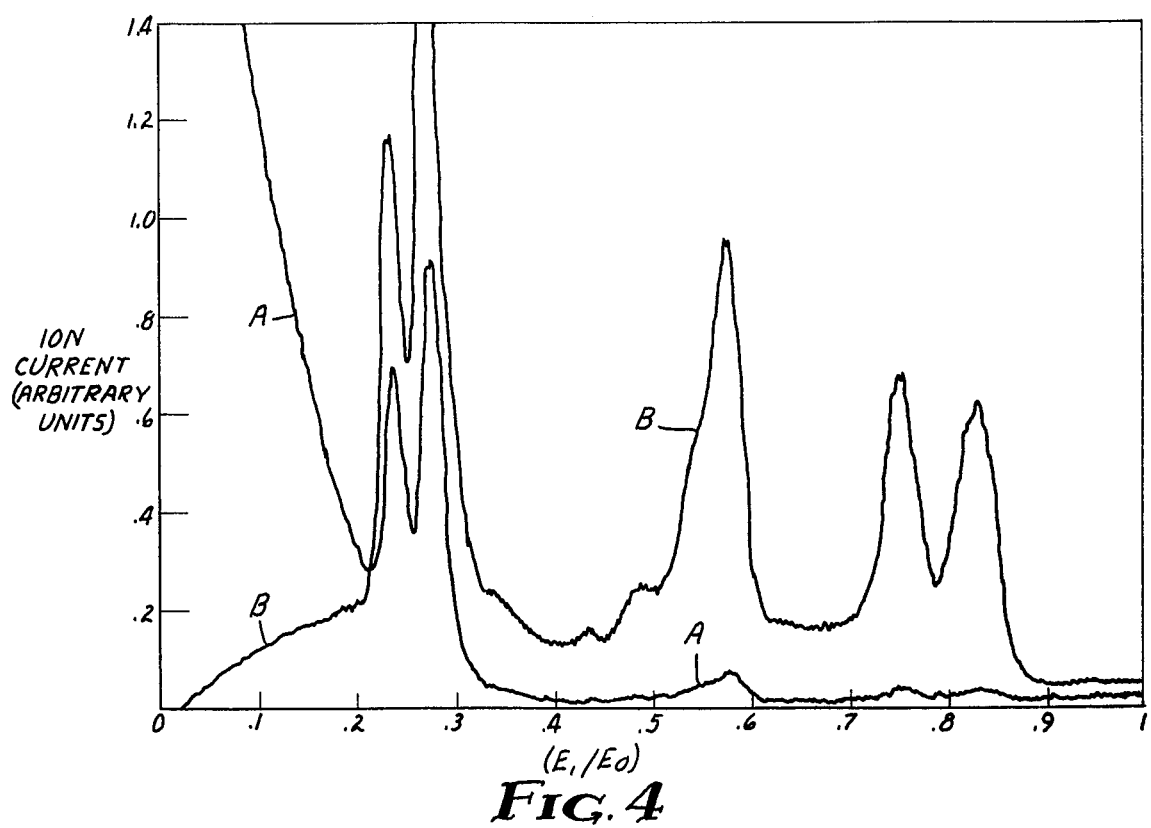

The spectra shown in FIGS. 3 and 4 are illustrative of data obtained with a spectrometer such as that shown in FIG. 2 with the exception that the metal screens 132, 134, 144 and 146 were omitted. The spectra of FIG. 3 were obtained by backfilling a chamber with a partial pressure of $3 \times 10^{-3}$ Pascal of helium. The ion gun was then energized to provide a beam of helium ions at an energy of 2.5 KeV at a beam current of approximately 60 nanoamps. This beam was then scattered from a specimen of Type AISI 300 series stainless steel and a display means such as an X-Y recorder was driven by the electronic signal from the electron detector 154 and by a signal derived from the analyzer power supply.

Prior art ion scattering spectrometers in which the input to the multiplier 152 is operated at a substantially negative potential such that the output may be at approximately ground potential and the electronic signal therefrom directly connected to subsequent amplifying circuits, typically yield data such as shown in curve A of FIG. 3. In that curve, it may be noted that a relatively low sensitivity to relatively high energy ions is present, such as the peaks at an $E_1/E_o$ ratio of 0.78 and 0.4. Furthermore, such spectra are typically characterized by a large intensity peak for values of $E_1/E_o$ ranging between 0 and 0.2, which is generally attributed to the presence of sputtered ions.

The improvement of the present invention, wherein in the embodiment in which the input to the multiplier 152 is operated at substantially ground potential and the output of the multiplier at a substantially positive potential with respect to ground such that the output signal is capacitively coupled to subsequent amplifying circuits, produces a significantly improved spectrum shown in curve B of FIG. 3. In that spectrum, it may be noted that the overall intensity of the scattered ion peaks has been increased by nearly an order of magnitude, while the low energy peak generally attributed to the presence of sputtered ions is nearly totally absent. These vastly improved results are believed due to at least two factors. The first result i.e., the overall increase in intensity of the spectral peaks, is believed to relate to the relative potentials at the exit aperture of the analyzer, such as the exit diaphragm 48 of FIG. 1 or the aperture plate 148 of FIG. 2, and the potential at the entrance portion of the multiplier, such as multiplier 62 of FIG. 1 or multiplier 152 of FIG. 2. In conventional prior art ISS systems, the exit aperture has heretofore been maintained at approximately ground potential and the entrance to the multiplier at several thousand volts negative with respect to ground such that the output of the multiplier is approximately at ground potential. This results in a strong electric field between these members and is now believed to result in the extraction of significant quantities of secondary electrons from the entrance surface of the multiplier toward the exit from the analyzer, rather than promoting the collection of such electrons into the multiplier where they contribute to the avalanche of secondary electrons.

In contrast, in the present invention, the exit diaphragms or apertures and the entrance to the multiplier are maintained at substantially the same potential such that the secondary electrons produced at the entrance to the multiplier are principally influenced only by the field applied to the multiplier, and cause the secondary electrons to drift into the multiplier and contribute to the avalanche of secondary electrons. The resultant increased signal is illustrated in curves B of both FIGS. 3 and 4, wherein the intensity of the high energy portion of the spectra may be seen to be approximately one order of magnitude greater in intensity.

The second result afforded by the present invention, i.e., the near elimination of the low energy peak, is believed to relate to factors affecting the ions traversing the analyzer. In prior art ISS devices, when the analyzer is adjusted to pass low-energy ions, ions having an energy nominally outside the pass-band of the analyzer are attracted by the field through the exit section to the detector. In the present invention, the elimination of the field ensures that only focused ions having a selected energy and hence an appropriate trajectory through the exit section of the analyzer are received by the detector.

Furthermore, in the present invention, low-mass scattered ions are detected in preference to high-mass sputtered ions, since the energy of the incident ions is controlled by the lower applied potential on the detector to fall into the range of energies for which there is an appreciable variation in the efficiency with which secondary electrons are produced in response to ion bombardment as a function of the mass of the ion. This biasing thus allows the utilization of what is an inherent property of surfaces, but which has heretofore been recognized only as a limitation. It is well known that yield of secondary electrons, i.e., the efficiency of a surface in producing secondary electrons in response to bombardment of that surface by charged particles, be they electrons, ions, etc., is dependent upon the mass and velocity, i.e., the energy, of the impinging particles. The yield in the production of secondary electrons typically is low for low velocity particles, passes through a peak, and decreases again for high velocity particles. The detection efficiency of a continuous channel electron multiplier is defined to be the ratio of the number of output charge pulses to the number of incident ions and is partially determined by the secondary electron yield of the electron emissive surface at the input.

In general, such multipliers are operated with a sufficiently high attractive potential on the input surface that the incident ions produce a sufficient number of secondary electrons to assure detection of the resulting pulse, i.e., the detector efficiency will be unity, and thus ensure detection. While the detection efficiency can never exceed unity regardless of how high the yield increases, the detection efficiency may decrease if the yield is sufficiently low. Typically, if the energy of the impacting particles is in excess of approximately 2 KeV, the detection efficiency as a function of energy is substantially constant. In prior art ISS systems, the potential existing between the exit aperture of the analyzer and the entrance to the multiplier results in the acceleration of the existing ions such that the ions impacting on the input surface of the multiplier had energies in excess of approximately 2,000 eV. Accordingly, any variation in the efficiency of the production of secondary electrons as a function of the ion energy was scarcely detectable. In contrast, in the present invention the entrance to the electron multiplier is intentionally maintained at a potential such that the incoming ions have a velocity for a given mass such that the efficiency in the production of secondary electrons varies appreciably, depending upon whether high-velocity low-mass ions, or low-velocity high-mass ions are received.

The low-mass high-velocity ions utilized to form the primary ion beam, which ions are subsequently scattered from the surface, are received on the electron multiplier surface at substantially the same energy as the high-mass low-velocity sputtered ions. Since both types of ions having the same energy pass through the energy analyzer, the difference in velocities results in a different efficiency in the production of secondary electrons. This selective detection of low-mass high-velocity sputtered ions is dramatically shown in the low energy portions of the spectra shown in FIGS. 3 and 4. For example, in FIG. 3, the prior art spectrum (curve A) may be seen to have a high intensity portion extending between a value of $E_i/E_o$ in the range of 0 to 0.2. Such a spectrum is believed to be due to the presence of sputtered ions and may be seen to be completely eliminated in the spectrum of the present invention (curve B).

Similarly, in FIG. 4, which spectra were obtained under the substantially identical conditions as those presented in FIG. 3, with the exception that a primary ion beam of neon, rather than helium was provided, the prior art spectrum (curve A) is characterized by a low-sensitivity high-energy portion and a very high-intensity low-energy portion extending between values $E_i/E_o$ between 0 to approximately 0.2. Further, in this curve, the presence of scattered ion peaks in the range from 0.2 to 0.3 is distorted by the rapidly increasing sputtered ion peaks. In contrast, in curve B of FIG. 4, when using the present invention, the sputtered ion portion of the spectrum is eliminated and the intensity of the scattered ions increases, just as in the high-energy portion of the curve. Furthermore, since a greatly enhanced peak-to-background ratio is present, signals of appreciably lower intensity may now be detected. In curve B of FIG. 4, the origins of the peaks at ratios of $E_i/E_o$ in excess of 0.4 has not been clearly identified.

It has further been found that if the emissive surface of the detector is biased slightly negative with respect to the exit section of the analyzer, i.e., such as up to $-30$ volts, but preferably approximately $-20$ volts, the advantages discussed hereinabove are still realized and that yet a further advantage is effected. When ion scattering spectrometers utilizing a cylindrical mirror analyzer are operated with the energy analyzer turned off, i.e., such that particles of zero energy may pass through, it has been observed that an anomalously high counting rate or "spike" in the output electron signal is produced. Because the range at which the spike occurs lies outside that in which useful spectral peaks normally occur, the spike has not presented any undue problems; however, the intensity of the spike may produce permanent damage resulting in decreased gain in the detector. It is now believed that this spike is due to secondary electrons which have passed through the analyzer and which impinge upon the detector. Since the emissive surface of the detector is sensitive to either electron or ion impact, these electrons may then produce the aforementioned spike. However, by negatively biasing the detector, it has been found that such electrons are deflected away from the detector such that the anomalous spike disappears.

In an alternative embodiment, rather than maintaining the exit aperture plate 148 and the entrance cone of the electron multiplier 152 of FIG. 2 at the same potential, the potentials on the respective members may be selected such that the energy of the ions passed through the exit aperture 150 is altered to result in the optimum detection of the relatively low-mass high-velocity sputtered ions in preference to the relatively high-mass low-velocity sputtered ions. In this way, the energy of the ions impinging on the emissive surface of the detector is altered to correspond to that at which the mass dependence of the emissive surface results in the maximum difference in the detection of low-mass high-velocity ions versus high-mass low-velocity ions. In so doing, at least two modes of operation are feasible.

In one mode, the analyzer potentials may be varied as discussed in conjunction with the description of FIG. 2 hereinabove, i.e., the potential on the inner electrode of the analyzer being held constant, such as at ground and the outer electrode varied to control the passage of ions having a selected energy. In this mode, the energy of the ions impinging upon the detector is altered to that corresponding to the optimum preferential detection by applying a suitable potential between the exit of the analyzer and the input to the detector.

In a second mode, the potential on the inner electrode of the analyzer is varied with respect to the potential at the target or first screen (132) in order to selectively pass ions of a given energy. The potential on the outer electrode of the analyzer is then varied to maintain a constant potential difference between the two electrodes such that the analyzer passes ions of a constant energy, which energy corresponds to that determined to result in the optimum desired preferential detection.

For example, in this second mode, positive ions, such as 2 KeV noble gas ions, are impinged on a specimen surface maintained at substantially ground potential, i.e., terminal 88 being coupled to a common ground. In order to maintain an equipotential between the specimen surface and the entrance portion of the analyzer, the screen 132 is maintained at ground potential. The selection of ions having a given scattered energy is then effected by applying a time varying potential on the inner cylinder 114, on the screen 131 and on the screen 134 (which are all electrically coupled together) over a range between $-2500$ volts and 0. Accordingly, at any given potential within that range, ions having an appropriate energy within a time varying range of energies will be allowed to pass through the screens and into the analyzer section 129 between the inner and outer cylindrical electrodes 114 and 116, respectively. In this embodiment, the outer electrode 116 is maintained at a constant +1250 volts potential with respect to the potential on the inner electrode 114. Accordingly, the potential on the outer electrode 116 is varied over a range of potentials from −1250 volts to −1250 volts in synchronization with the variation of the potential on the inner electrode 114 such that the analyzing section 129 sequentially passes ions having different initial scattered energies. Regarding the exit section of the analyzer, screens 142 and 146 are likewise electrically coupled to the inner cylinder 114. The potential on these screens therefore ranges between −2500 and 0 volts. In contrast, the potential on the final screen 144 and that on the exit aperture plate 148, which members are electrically coupled together, is varied over a range of −50 to +2450 volts, and the entrance to the electron multiplier is varied over a similar range such that the ions received all have a constant energy. The output of the multiplier is varied over a range of +1950 to +4450 volts. The variable sensitivity at the input of the multiplier to high-velocity low-mass ions is thus optimized. Both of these embodiments accordingly provide the advantages of a selectable constant energy resolution and band pass-width across the spectrum enabling more quantitative interpretation of the data, and allows one to optimize the mass dependence of the multiplier.

Having thus described the present invention, what is claimed is:

1. In an ion scattering spectrometer comprising
    (a) means for supporting a specimen, a surface of which is to be analyzed,
    (b) means for directing a beam of ions having a preselected atomic mass and a preselected energy toward the surface,
    (c) analyzing means comprising an entrance section for receiving ions from the surfaces, analyzing section for selecting such ions passing through the entrance section at a given angle as have a predetermined energy, and an exit section for passing said selected ions, and
    (d) detecting means comprising a material having an electron emissive surface for receiving and detecting passed ions from the analyzing means by converting an ion current associated with said passed ions into a corresponding electron signal,
    the improvement wherein the spectrometer further comprises (e) biasing means to control the energy of ions impinging upon the electron emissive surface, to result in
    (i) the preferential detection of low-mass scattered ions having relatively high velocities over high-mass sputtered ions having relatively low velocities,
    and for maintaining a potential on said electron emissive surface within 30 volts of that maintained on said exit section of the analyzer means resulting in
    (ii) the absence of a force tending to attract electrons emitted from the emissive surface toward the analyzing means, and
    (iii) the absence of a force tending to attract such ions having an energy outside the pass-band of the analyzer through the exit section of the analyzing means to the emissive surface, such that there is produced an appreciably stronger electron signal corresponding to scattered ions, and a corresponding reduction in the background of the electron signal corresponding to the detection of heavier sputtered ions and spurious scattered ions not within the pass-band of the analyzer, said detecting means further comprising means for indirectly coupling said electron signal from the output portion to an amplifier means operating near ground potential, such that said output section may be maintained at a positive potential to cause electrons emitted from said emissive surface to drift into the detecting means.

2. A spectrometer according to claim 1, wherein said biasing means further comprises means for maintaining a positive potential on an output portion of the detecting means with respect to the emissive surface to subject electrons emitted from the emissive surface to an electric force field to cause the electrons to drift into the detecting means and away from the analyzing means to thereby ensure that most of the emitted electrons contribute to the production of the resultant electron signal corresponding to an ion current of a given intensity.

3. A spectrometer according to claim 1, wherein said biasing means comprises means for maintaining the emissive surface and the exit section of the analyzing means at the same potential.

4. A spectrometer according to claim 3, wherein said biasing means maintains the emissive surface and the exit section at ground potential.

5. In an ion scattering spectroscopic method for investigating the composition of a surface of a material comprising the steps of
    (a) supporting a specimen, the composition of a surface of which is to be analyzed,
    (b) directing a beam of ions having a preselected atomic mass and a preselected energy toward the surface,
    (c) analyzing ions received from the surface by passing ions received from the surface at a given angle through an entrance section, by subsequently selecting ions having a predetermined energy in an analyzer section and passing the selected ions through an exit section, and
    (d) detecting the passed ions in a detecting means comprising a material having an electron emissive surface by impinging the passed ions on the emissive surface and converting an ion current associated therewith into a corresponding electron signal,
    THE IMPROVEMENT WHEREIN the method further comprises the step of
    (e) biasing said emissive surface to control the energy of ions impinging on the emissive surface, resulting in
    (i) the preferential detection of low-mass scattered ions having relatively high velocities over high-mass sputtered ions having relatively low velocities, and to maintain a potential thereon within 30 volts of that maintained on said exit section resulting in
    (ii) the absence of a force tending to attract electrons emitted from the emissive surface toward said exit section, and
    (iii) the absence of a force tending to attract such ions having an energy outside the pass-band of the analyzer through the exit section toward the emissive surface, such that there is produced an appreciably stronger electron signal corresponding to scattered ions, and a corresponding reduction in the background of the electron signal corresponding to the detection of heavier sputtered ions, and spurious scattered ions not within the pass-band of the analyzer.

6. A spectroscopic method according to claim 5, further comprising maintaining a positive potential on an output portion of the detecting means with respect to said emissive surface to cause electrons emitted from that surface to drift in an electric force field away from said exit section and into the detecting means to thereby ensure that most of the emitted electrons contribute to the production of the resultant electron signal corresponding to an ion current of a given intensity.

7. A spectroscopic method according to claim 5, comprising maintaining said emissive surface and said exit section at the same potential.

8. A spectroscopic method according to claim 5 comprising maintaining said emissive surface and said exit section at ground potential.

9. A spectroscopic method according to claim 5 comprising maintaining said emissive surface approximately 20 volts negative with respect to said exit section such that electrons passed through the exit section are repelled from the emissive surface.

10. A spectroscopic method according to claim 5 comprising applying a varying bias to said emissive surface and to said exit section to maintain the energy of ions impinging on said emissive surface at a constant value regardless of the manner in which other potentials may be applied to control said passed ions.

* * * * *